United States Patent [19]

Schulz et al.

[11] 4,245,101
[45] * Jan. 13, 1981

[54] METHOD OF PREPARATION AND USE OF N-PHENYL-N'-1,2,3-THIADIAZOLE-5-YL-THIOUREA

[75] Inventors: Heinz Schulz; Friedrich Arndt, both of Berlin, Fed. Rep. of Germany

[73] Assignee: Schering Aktiengesellschaft, Berlin and Bergkamen, Fed. Rep. of Germany

[*] Notice: The portion of the term of this patent subsequent to May 13, 1992, has been disclaimed.

[21] Appl. No.: 468,031

[22] Filed: May 8, 1974

[30] Foreign Application Priority Data

May 14, 1973 [DE] Fed. Rep. of Germany ....... 2324732

[51] Int. Cl.³ ................... A01N 47/36; C07D 285/06

[52] U.S. Cl. ......................................... 548/127; 71/76; 71/78; 71/90

[58] Field of Search ................ 260/306.8 D; 548/127

[56] References Cited

U.S. PATENT DOCUMENTS

| | | | |
|---|---|---|---|
| 3,565,901 | 2/1971 | Cebalo | 260/299 |
| 3,787,434 | 1/1974 | Volpp et al. | 260/306.8 D |
| 3,830,641 | 8/1974 | Volpp | 260/306.8 D |
| 3,883,547 | 5/1975 | Schulz et al. | 260/306.8 D |

*Primary Examiner*—Alton D. Rollins
*Attorney, Agent, or Firm*—Michael J. Striker

[57] ABSTRACT

The specification discloses methods for the preparation and use of the compound N-phenyl-N'-1,2,3-thiadiazole-5-yl-thiourea in the regulation and control of plant growth.

1 Claim, No Drawings

METHOD OF PREPARATION AND USE OF N-PHENYL-N'-1,2,3-THIADIAZOLE-5-YL-THIOUREA

This invention is directed to the control and regulation of plant growth and more specifically to N-phenyl-N'-1,2,3-thiadiazole-5-yl-thiourea and the employment of this compound in compositions and methods for the control and regulation of plant growth.

The control of plant growth which can extend to total inhibition of growth is an important techninque in agriculture not only with respect to weeds but also for crop plants. It is often of value to retard vegatative growth of the overall plant or to inhibit growth of only certain portions of the plant. For example promotion of bud growth while inhibiting the development of side shoots is frequently a desirable technique in the production of leaf plants such as tobacco. In general many advantageous benefits can be obtained through the use of the compound to promote growth of stem-buds in plants such as Gramincae.

An object of this invention is to provide a method for producing N-phenyl-N'-1,2,3-thiadiazole-5-yl-thiourea. Another object of the invention is to provide an agricultural agent which can be used to regulate and control vegetative growth. Still another object of the invention is to provide methods for the selective control of the development or growth of various parts of plants e.g., roots, stems, side shoots, buds, and the like. A further object is to provide a versatile agricultural agent which can be formulated into compositions for application to plants and seeds, which compositions can also contain, as desired, other herbicides, fungicides, fillers, and suitable agricultural chemicals. Another object is to provide a method for inhibiting plant growth and causing development of a dark green leaf coloration.

These and other related objects are achieved by providing according to the herein described reactions the compound N-phenyl-N'-1,2,3-thiadiazole-5-yl-thiourea and compositions containing the compound which can be applied to plants and seeds by known procedures. Accordingly, it is possible to inhibit plant growth while promoting bud formation. The range of effects achievable extends from a complete herbicidal effect through dwarf growth to a full and vigorous condition of growth. The compound is suitable and effective in both pre- and post-emergence methods of treatment as well as for methods using seed-dusting techniques.

In one aspect thereof the instant invention comprises a method for the regulation of plant growth by applying to the plants, either post emergence or pre-emergence, a growth regulating amount of N-phenyl-N'-1,2,3-thiadiazole-5-yl-thiourea. The term growth regulating amount refers to any amount effective for the regulation or control, by way of inhibition or promotion, of the normal growth patterns of the plants whether they be designated as weeds or crop plants.

More specifically the method comprises application of the compound, preferably in combination with a carrier or vehicle to the plants at a rate of application sufficient to supply from about 0.1 to about 10. kilograms of the compound per hectare depending on the effect desired.

The compound of this invention can be prepared by reacting 5-amino-,1,2,3-thiadiazole having the formula

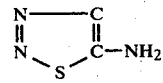

with either thiocarbanilic acid chloride in the presence of an acid acceptor such as an organic or inorganic base. An amine such as triethylamine is suitable. Alternatively, the thiadiazole can be reacted with a chlorothioformic acid ester having the formula

CL—CS—OR wherein R is a lower alkyl radical i.e., one having from 1 to 5 carbon atoms, preferably 1 to 3 carbon atoms. This reaction forms a N-(1,2,3-thiadiazole-5-yl) thiocarbamidic acid-o-alkyl ester which then is reacted with aniline. A third method involves use of thiophosgene in place of thiacarbanilic acid in the presence of inorganic acid acceptors e.g., calcium carbonate, magnesium oxide, and the like. The resulting N-(1,2,3-thiadiazole-5-yl) thiocarbamoyl chloride or thiadiazoleisothiocyanate can be reacted with aniline in the presence of catalytic quantities of triethylamine. Another method employs phenylisohiocyanate in place of the thiocarbanilic acid chloride, the reaction being carried out in the presence of catalytic amounts of an organic base such as triethylamine.

In all the cases the reactions and recovery of products are in accordance with usual techniques and procedures. Starting materials for the above reaction are known and can be prepared by known reactions.

In order to achieve the desired regulatory effect the compound is applied to the plants either post- or pre-emergently in amounts ranging from about 0.1 to about 10 kilograms per hectare. At a rate of application of about 10 kg. per hectare total inhibition approaching a herbicidal effect is achieved. For most regulatory situations the promotion of bud growth can be achieved with applications of from about 0.1 to about 5 kg. per hectare. The actual amounts to be used can be easily arrived at by simple observation of results and adjustment of the rate of application according to the desired effect. Good results by seed dusting can be obtained with about 0.1 grams of the compound per 100 kilograms of seed.

The compound is generally applied by usual techniques for the application of agricultural chemicals. For example water can be used as a vehicle for spray solutions containing the active ingredient. Solutions can be applied at rates ranging from about 100 to 1000 liters per hectare. The larger volumes and more concentrated formulations being appropriate for total weed control. In general the compound is present in the formulation in amounts ranging from about 20 to about 80 weight percent, the balance being a suitable carrier or vehicle and if desired a surface active agent. The surface active agent is usually present in amounts up to about 20 weight percent.

The active ingredient can be applied in various types of formulations such as powders, scatters, granulates, solutions, emulsions, or suspensions for which application techniques are well known. In addition to the compound of this invention the formulations can contain compatible wetting agents, adhesives, dispersing aids, emulsifiers, and other suitable adjuvants.

Liquid vehicles with which the active compound can be admixed for purposes of facilitating application include water, alyshatic and aromatic hydrocarbons such as benzene, toluene, cyclohexanone, isophorone and the like and mineral oil fractions.

Solid vehicles generally useful in the formulation and application of herbicides and other agricultural chemicals include mineral earths, e.g., silicious clay, silica gel, talc, kaolin, attaclay, limestone, and silica. Plant products such as flour can also be used.

It is often expedient to employ surface active agents in the formulations in order to improve and facilitate distribution to the plants. Suitable surface active agents include calcium-lignin sulfonate, the polyoxyethyleneoctylphenol ethers, naphthalene sulfonic acids, phenol sulfonic acids, formaldehyde condensates, fatty alcohol sulfates, and fatty acid salts of alkali and alkaline earth metals.

The agricultural formulations and compositions disclosed herein can be conveniently prepared by simple admixture of the selected ingredients by well known techniques. The compositions can be prepared in advance or immediately prior to use.

The following examples illustrate the principles and practice of the invention which has been found applicable to a wide variety of plants including species of the families Gramincae, Concolculaceae, Cruciferae, Umbellifers, Labiates, Solanaceae, Rubiaceae, Composites, and Cucurbitaceae.

EXAMPLE 1

10.1 g (0.1 mole) 5-amino-1,2,3-thiadiazole in 75 ml of tetrahydrofurane, 11.95 ml (0.1 mole) phenylisothiocyanate and 3 drops triethylamine are heated with refluc for 4 hours. After standing overnight, the precipitated crystals are suction-filtered, washed with some tetrahydrofurane/benzene, and dried under vacuum. Yield: 6.7 g (28.4% of the theory), m.p.: 205° C. (decomposition).

The compound does not dissolve in water or aliphatic or aromatic hydrocarbons. It is soluble in polar organic solvents such as acetone, cyclohexanone, isophorone, dimethyl sulfoxide and dimethyl formamide.

The starting products for the production of the compound according to the invention are known and can be prepared by known methods.

EXAMPLE 2

Oat plants in the 20 leaf stage, potted or grown in bowls, were treated in the greenhouse with aqueous suspensions of spray powders containing 20% of the compounds listed in the table. The compounds were in the form of aqueous suspensions, which were applied at 500 liters/ha. The compound according to the invention was applied in a quantity of 0.3 kg active substance per hectare, the comparison agent in a quantity of 1.0 kg active substance per hectare.

Two weeks after the treatment, the number of formed side shoots was determined. Despite the larger quantity used, no bad-promoting effect was obtained with the comparison agent.

| Compound of invention | Kg active substance per hectare | Oats No. of stem buds per 100 plants |
|---|---|---|
| N-phenyl-N'-1,2,3-thiadiazole-5-yl-thiourea | 0.3 | 113 |
| Comparison agent (1,2-dihydropyridazine-3,6-dione) | 1 | 0 |
| Untreated control | — | 0 |

EXAMPLE 3

In the greenhouse, potted peanut plants in the two-to-three-leaf stage were treated with the compound of the invention. The quantities used were 0.3, 1 and 3 kg active substance/ha, the compound being applied as a spray powder in aqueous suspension at 500 liter/ha. The growth delaying effect was determined by length measurement of the first axial member (internode). The measurement results are stated as percentual growth retardation in comparison to Untreated.

| Compound of invention | Kg active substance/ha | Growth retardation in % |
|---|---|---|
| N-phenyl-N'-1,2,3-thiadiazole-5-yl-thiourea | 0.3 | 60 |
| | 1 | 84 |
| | 3 | 84 |
| Untreated control | — | 0 |

In the greenhouse, the compound of the invention was applied in a quantity of 0.3 kg active substance as spray powder in 500 liter of aqueous suspensions per hectare before and after emergence of the plant species listed in the following table. As comparison agent, 1,2-dihydropyridazine-3,6-dione in aqueous solution was sprayed in the same quantity and at the same time of application. In the following table the growth inhibition is shown 3 weeks after the treatment in % referred to Untreated. As the findings show, a much stronger inhibiting effect was obtained with the compound of the invention than with the comparison agent.

| | Growth inhibiition in % referred to Untreated | | | | | | | |
|---|---|---|---|---|---|---|---|---|
| | Pre-emergence | | | | Post-emergence | | | |
| | A | B | C | D | A | B | C | D |
| Cauliflower | 0.3 | 100 | 80 | 0 | 0.3 | 100 | 0 | 0 |
| Sugar beet | 0.3 | 0 | 0 | 0 | 0.3 | 60 | 0 | 0 |
| Tomato | 0.3 | 0 | 0 | 0 | 0.3 | 0 | 0 | 0 |
| Carrot | 0.3 | 100 | 50 | 0 | 0.3 | 50 | 20 | 0 |
| Onion | 0.3 | 100 | 0 | 0 | 0.3 | 50 | 0 | 0 |
| Cucumber | 0.3 | 10 | 10 | 0 | 0.3 | 50 | 0 | 0 |
| Alfalfa | 0.3 | 70 | 20 | 0 | 0.3 | 50 | 20 | 0 |
| Spinach | 0.3 | 50 | 50 | 0 | 0.3 | 80 | 20 | 0 |
| Bush bean | 0.3 | 20 | 20 | 0 | 0.3 | 20 | 0 | 0 |
| Cotton | 0.3 | 0 | 0 | 0 | 0.3 | 50 | 0 | 0 |
| Soy bean | 0.3 | 100 | 50 | 0 | 0.3 | — | — | — |
| Potato | 0.3 | 0 | 0 | 0 | 0.3 | 0 | 0 | 0 |
| Corn | 0.3 | 10 | 0 | 0 | 0.3 | 0 | 0 | 0 |
| Wheat | 0.3 | 0 | 0 | 0 | 0.3 | 0 | 0 | 0 |
| Barley | 0.3 | 0 | 0 | 0 | 0.3 | 0 | 0 | 0 |
| Oat | 0.3 | 0 | 0 | 0 | 0.3 | 0 | 0 | 0 |
| Rice | 0.3 | 0 | 0 | 0 | 0.3 | 10 | 0 | 0 |
| Pea | 0.3 | 0 | 0 | 0 | 0.3 | 70 | 0 | 0 |
| Narrow-stem kale | 0.3 | 70 | 40 | 0 | 0.3 | 70 | 0 | 0 |
| Stellaria media (Chickweed) | 0.3 | 90 | 0 | 0 | 0.3 | 60 | 0 | 0 |
| Senecio Vulgaris | | | | | | | | |

-continued

Growth inhibiition in % referred to Untreated

| | Pre-emergence | | | | Post-emergence | | | |
|---|---|---|---|---|---|---|---|---|
| | A | B | C | D | A | B | C | D |
| (groundsel) *Matricaria chamomilla* (True chamomile) | 0.3 | 20 | 0 | 0 | 0.3 | 0 | 0 | 0 |
| | 0.3 | 100 | 100 | 0 | 0.3 | — | — | — |
| *Lamium amplexicaule* (Dead Nettle) | 0.3 | 0 | 0 | 0 | 0.3 | 10 | 10 | 0 |
| *Centaurea cyanus* (Cornflower) | 0.3 | — | — | — | 0.3 | 20 | 0 | 0 |
| *Amarantus retroflexus* (Amaranth) | 0.3 | 40 | 0 | 0 | 0.3 | 90 | 10 | 0 |
| *Chrysanthemum segetum* (Corn marigold) | 0.3 | 90 | 0 | 0 | 0.3 | 20 | 0 | 0 |
| *Alopesurus myosuroides* (Foxtail) | 0.3 | 50 | 0 | 0 | 0.3 | — | — | — |
| *Setari faberi* (American millet) | 0.3 | 20 | 0 | 0 | 0.3 | — | — | — |

A = kg active substance/ha;
B = Compound of invention, N-phenyl-N'-1,2,3-thiadiazole-5-yl-thiourea;
C = Comparison agent, 1,2-dihydropyridazine-3,6-dione;
D = Untreated

What is claimed is:
1. N-phenyl-N'-1,2,3-thiadiazol-5-yl-thiourea.